United States Patent [19]
Wiebe

[11] Patent Number: 4,720,507
[45] Date of Patent: Jan. 19, 1988

[54] BIOLOGICAL CONTRACEPTIVE AND CONTRACEPTIVE TECHNIQUE FOR MALES

[75] Inventor: John P. Wiebe, London, Canada

[73] Assignee: University of Western Ontario, London, Canada

[21] Appl. No.: 586,258

[22] Filed: Mar. 5, 1984

[51] Int. Cl.$^4$ ............................................ A61K 31/045
[52] U.S. Cl. ........................................ 514/738; 514/841
[58] Field of Search ........................... 424/343; 514/738

[56] References Cited

U.S. PATENT DOCUMENTS 4,156,427  5/1979  Fahim ................................. 128/215
4,356,189 10/1982  Stagg et al. ........................ 424/317

FOREIGN PATENT DOCUMENTS 1189789  7/1985  Canada ............................... 167/135

OTHER PUBLICATIONS

Remington—Pharmaceutical Sciences, 1980, p. 1255.
Lachman et al.—The Theory & Practice of Industrial Pharmacy, 2nd Ed., 1976, pp. 586–589.
Chemical Abstracts, 77:14938p, (1972).

Primary Examiner—Leonard Schenkman
Attorney, Agent, or Firm—R. Craig Armstrong

[57] ABSTRACT

A male contraceptive preparation and a contraceptive technique are disclosed. The contraceptive preparation consists essentially of 1,2,3-trihydroxypropane ("THP"; glycerol) in solution in a suitable carrier such as distilled water or saline solution. In accordance with the contraceptive technique, the contraceptive preparation is injected into the testes. The THP has been found to act as a potent inhibitor of spermatogenesis, resulting in long term infertility, with no apparent effect on libido, secondary sex characters, mating behavior and hormone levels. There are no observed side effects and no observed effects on other aspects of reproductive and hormonal biology.

9 Claims, 7 Drawing Figures

BIOLOGICAL CONTRACEPTIVE AND CONTRACEPTIVE TECHNIQUE FOR MALES

BACKGROUND OF THE INVENTION

1. Field of the Invention

This invention relates generally to contraception, and specifically to a biological contraceptive and contraceptive technique for males.

In the case of humans, overpopulation remains one of the most critical problems facing humankind. In recent times, the contraceptive pill has been successfully employed by women to prevent ovulation and conception. However, the contraceptive pill designed for use by women consists of steroids (a mixture of progestagens and estrogens) and there is considerable concern about its potentially harmful side-effects following prolonged use. There is thus at present considerable pressure to block the reproductive capacity in the male and to not place all the chemical and psychological burden on the female.

Methods of male fertility control are also highly desireable in the case of animals, especially as simpler alternatives to the present procedures of castration or other forms of surgical sterilization.

An ideal chemical contraceptive for the male would be one which effectively arrests spermatogenesis (i.e. stops formation of sperm cells) or blocks the fertilizing capacity of sperm, without affecting testicular steroidogenesis (production of male steroid hormones), libido, accessory sex glands, and pituitary function, in the absence of toxic or other undesireable side effects. The procedure would be simple, non-surgical, and preferably expose only the sperm producing tissue to the compound, thus avoiding distribution of foreign chemicals to non-reproductive tissues in the body. Infrequent application of the treatment would also be desirable.

2. Description of the Prior Art

An "ideal" male contraceptive agent has not been described in the prior art, although many compounds have been explored for the purpose of inhibiting or arresting spermatogenesis (see Bennett, J. P. (1974), *Chemical Contraception*, Columbia Press, New York, pp. 133–170; Davies, A. G. (1980), *Effects of Hormones, Drugs and Chemicals on Testicular Function*, Vol. 1, Eden Press, Westmount, pp. 123–164; and Jeffcoate, S. L. and Sandler, M. (Editors), *Progress Towards a Male Contraceptive*, John Wiley and Sons, Chichester, 1982). While many of the compounds tested in the past possess some anti-spermatogenic or anti-fertilizing capacity, their contraceptive action is invariably overshadowed by their cytotoxic, neurotoxic or anti-metabolic effects, or by their untoward effects on libido, accessory sex glands and the male endocrine system (see Jeffcoate and Sandler, supra). Moreover, the compounds that have been tested generally require fairly large daily doses and their long range effects remain unknown (see Shandilya, L., Clarkson, T. B, Adams, M. R., and Lewis, J. C. (1982), "Effects of gossypol on reproductive and endocrine functions of male cynomolgus monkeys (*Macaca fascicularis*)", Biol.Reprod. 27:241–252).

Vasectomy is of course a proven technique, but it requires surgery, albeit relatively minor surgery. Epididymal sperm congestion and sperm cysts and sometimes autoimmune reactions are observed.

Although castration will effectively remove sperm production, it also removes the source of male sex steroid hormones and as such is unacceptable for human males. Castration is often employed on pets and farm animals, but it requires aseptic surgery and a period of healing and thus is relatively complicated.

SUMMARY OF THE INVENTION

It is an object of the invention to provide a contraceptive and contraceptive technique for males which offers advantages over those known in the prior art.

In accordance with the present invention there is provided a contraceptive preparation intended for injection into the testes, consisting essentially of 1,2,3-trihydroxypropane ("THP"; glycerol) in a solution.

There is further provided a method of contraception comprising preparing the solution, and then injecting a quantity into the testes.

BRIEF DESCRIPTION OF THE DRAWINGS

The invention will now be described in greater detail, with reference to tables included in the specification and with reference to the accompanying drawings, in which.

DESCRIPTION OF THE PREFERRED EMBODIMENT

Figure 1A:
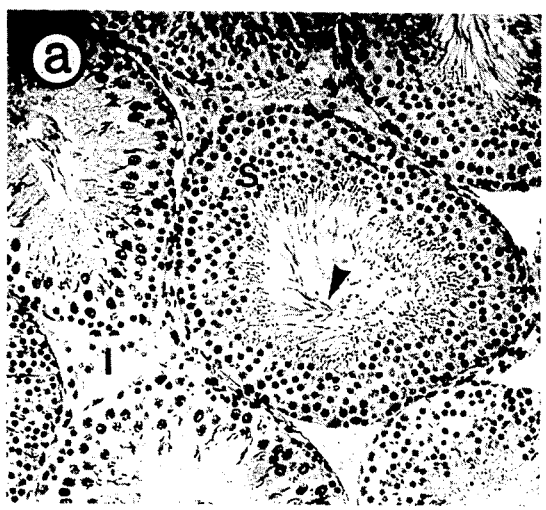
FIG. 1 is a set of photographs of cross-sections of seminiferous tubules from testes of control (FIG. 1 (*a*)) and treated (FIG. 1 (*b*)) rats.

The present invention involves a single intratesticular injection with a solution comprised of components found in most living cells, i.e. components which are not foreign to the body, and are non-toxic and nonhormonal substances.

The preferred procedure is essentially as follows. A solution is prepared consisting of saline/1,2,3-trihydroxypropane ("THP"; glycerol) (3:7), or saline/THP/ethanol (3:7:0.25), or distilled water/THP (3:7), or distilled water/THP/ethanol (3:7:0.25). The proportions of water to THP can be varied, as it is the THP which has the antispermatogenic action.

The solution is then sterile filtered (0.2 micron filter units) into sterile serum vials. The scrotal area is cleaned with 95% alcohol. Injections are then made into the approximate center of the testis.

In rats, 50 to 200 microliters per testis has been found to be sufficient to block spermatogenesis for at least 21 weeks. A total of ten experiments comprising over 200 rats and one experiment with 24 hamsters have been conducted to test the effectiveness of the procedure. Preliminary conclusions from the most recent experiments are that an equivalent of 25 microliters at the above ratios is also effective, and experimentation involving still lower concentrations is in progress.

EXAMPLES

Sprague-Dawley rats were injected intratesticularly with a sterile-filtered solution of either A (THP/double distilled water/ethanol, 7:3:0.25) or B (double distilled water or water/ethanol), the former rats being hereinafter referred to as "Treateds" and the latter as "Controls". For the treatments, the rats were lightly anesthetized with ether, the scrotum was wiped with alcohol, and the solution was injected directly into the approximate center of the testes via a gauge 27 needle. Histological, biochemical and fertility determinations were made periodically after the injections.

In one experiment, 50 microliters of solution A was injected into the right testis of 48 day old rats. A week later, the injection was repeated. After one more week, i.e. two weeks after the first injection, the weights of the right testes were significantly less than the weights of the left testes (e.g. 0.415±0.028 g. versus 1.039±0.067 g.). Histologically, the seminiferous tubules in the right testes were devoid of germinal cells but the interstitial cells appeared normal. The reduced weights persisted at least 11 weeks after treatment.

In several subsequent experiments, the testes of 88-97 day old rats were injected once a week for 5 weeks, both with either solution A or B. Steroidogenesis, steroid enzyme activity, secondary sex characters, testicular histology and sexual behaviour were examined one week after the third and fifth injections and four weeks after the fifth injection. Homogenates from A-treated testes metabolized significantly more 14C-progesterone into 14C-labelled 17alpha-OH-progesterone, 20-alpha-dihydroprogesterone, androstenedione and testosterone on a per milligram protein basis than the B-treated ones. However, the steroidogenic activity on a per testis basis did not differ between Treateds and Controls. Seminal vesicles and prostate weights were not affected by the treatments, although the ratios of gonad to body weights ($\times 100$) were reduced from 0.67±0.06 in Controls to 0.34±0.03 in Treateds. Treateds and Controls showed the same level and degree of mating behaviour when caged with virgin females. Four weeks after the fifth injection, the epididymal sperm counts numbered $9.9 \times 10^5$ ($\pm 3.5 \times 10^5$) and $7.5 \times 10^7$ ($\pm 5.3 \times 10^7$) in the Treateds and Controls respectively.

In a number of subsequent experiments, rats were given only a single injection into each testis and histological, biochemical, and fertility determinations were made for up to 21 weeks after the injection. The results showed that within one week of the injection with THP, spermatogenesis had been arrested and within 2 weeks the seminiferous tubules were largely depleted of spermatogenic (sperm producing) cells; they remained devoid of dividing germ cells for the remainder of the experimental period. On the other hand, the Leydig (androgen producing) cells had a normal morphological appearance. Histochemical and biochemical studies showed that the activities of steroid enzymes (3-beta-hydroxysteroid dehydrogenase, 3-alpha-hydroxysteroid dehydrogenase, 17-beta-hydroxysteroid oxidoreductase, 17-alpha-hydroxylase, and $C_{17-20}$-lyase) involved in the androgen production, the in vitro conversion of 14C-progesterone, and the production of testosterone and androstenedione were not altered by the THP treatment. Similarly, the blood serum levels of testosterone and pituitary gonadotropins (LH and FSH), and the weights of the androgen-dependent prostate gland and seminal vesicles were the same as in the Controls. THP treated males showed the same level of sexual behaviour and mated with virgin females at the same frequency as Controls but all were infertile after the 3rd mating and remained 100% infertile for the duration of the experiments (21 weeks). The total number of sperm stored in the epididymides of treated rats declined rapidly and was reduced by 99.99% (of Controls' numbers) after the third mating.

The results of a number of such experiments will now be set out in greater detail.

Table 1 below shows the effects of THP treatment on the weights of testes, epididymides, prostate and seminal vesicles, and on the number of sperm in the epididymides, from one of the experiments. The results were similar in each of the other experiments where time of treatment, age of rats, and number of injections had been different. Table 1 shows that the weights of the Treated testes were significantly reduced one week after a single injection, and had declined to 46% and 37% of the Control testes weights by 2 and 11 weeks respectively. In the same experiment, the weights of the epididymides were significantly reduced in animals sampled 1, 2, and 11 weeks after the injection. The average number of sperm in each epididymis, following three matings, was reduced by 99.99% in the Treated animals. On the other hand, the weights of the accessory sex structures (prostate and seminal vesicles) were not affected by the treatment.

TABLE 1

Effects of THP Treatment on Weights of Testes and Accessory Structures and on Epididymal Sperm Number

| Tissue | Weeks after injection | Control(g) | Treated(g) |
|---|---|---|---|
| Testis | 1 | 3.24 ± .25 | 2.07 ± .19 |
|  | 2 | 3.35 ± .06 | 1.55 ± .07 |
|  | 11 | 3.31 ± .12 | 1.24 ± .04 |
| Epididymis | 1 | 1.33 ± .13 | .92 ± .04 |
|  | 2 | 1.33 ± .09 | .93 ± .07 |
|  | 11 | 1.35 ± .07 | .91 ± .08 |
| Prostate | 11 | 0.83 ± .08 | .81 ± .10 |
| Seminal vesicle | 11 | 1.55 ± .07 | 1.52 ± .09 |
| Total sperm in epididymis after 3 matings | 11 | $25.85 \times 10^7$ ($\pm 2.69 \times 10^7$) | $9.9 \times 10^3$ ($\pm 6.8 \times 10^3$) |

Twenty-four male rats, 85–91 days old (325–350 g) at the start of the experiment. Each testis injected with 200 microliters of sterile-filtered distilled water (Controls) or THP/water (7:3) (Treated) on day one. Animals were sampled 1, 2, and 11 weeks later. Each value represents the mean ± SEM obtained from tissues of 3–5 animals.

Figure 1B:
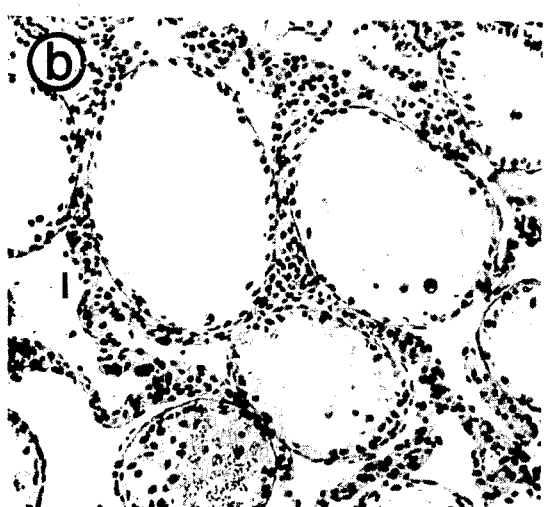

The photographs of FIG. 1 show the suppressive effects of THP treatment on gametogenesis. The effect appears to be rapid and highly selective, so that just 2 weeks after an injection, many seminiferous tubules are essentially empty of spermatogenic cell stages and spermatozoa, being lined only with normal appearing Sertoli cells and occasional primary germ cells. The interstitial Leydig cells, on the other hand, which are the primary source of testicular androgens, do not appear to be affected by the treatment. Both photographs are cross-sections of seminiferous tubules from rat testes, with a magnification of 180, 14 days after injection with distilled water (FIG. 1a) and THP/water (7:3) (FIG. 1b). Different stages of spermatogenic cells S are seen within the tubules and spermatozoa reside in the lumen (arrow), indicating normal progresssion of spermatogenesis in the control testes (FIG. 1a). The tubules from the treated testes (FIG. 1b) are devoid of spermatogenic cells, being lined only with Sertoli cells and some primary germ cells. The apparent increase in interstitial cells I is probably due to the marked decrease in seminiferous tubule diameter. Steroidogenic studies support the view that there has not been an increase in Leydig cell number nor a change in total steroidogenic activity.

Figure 2:
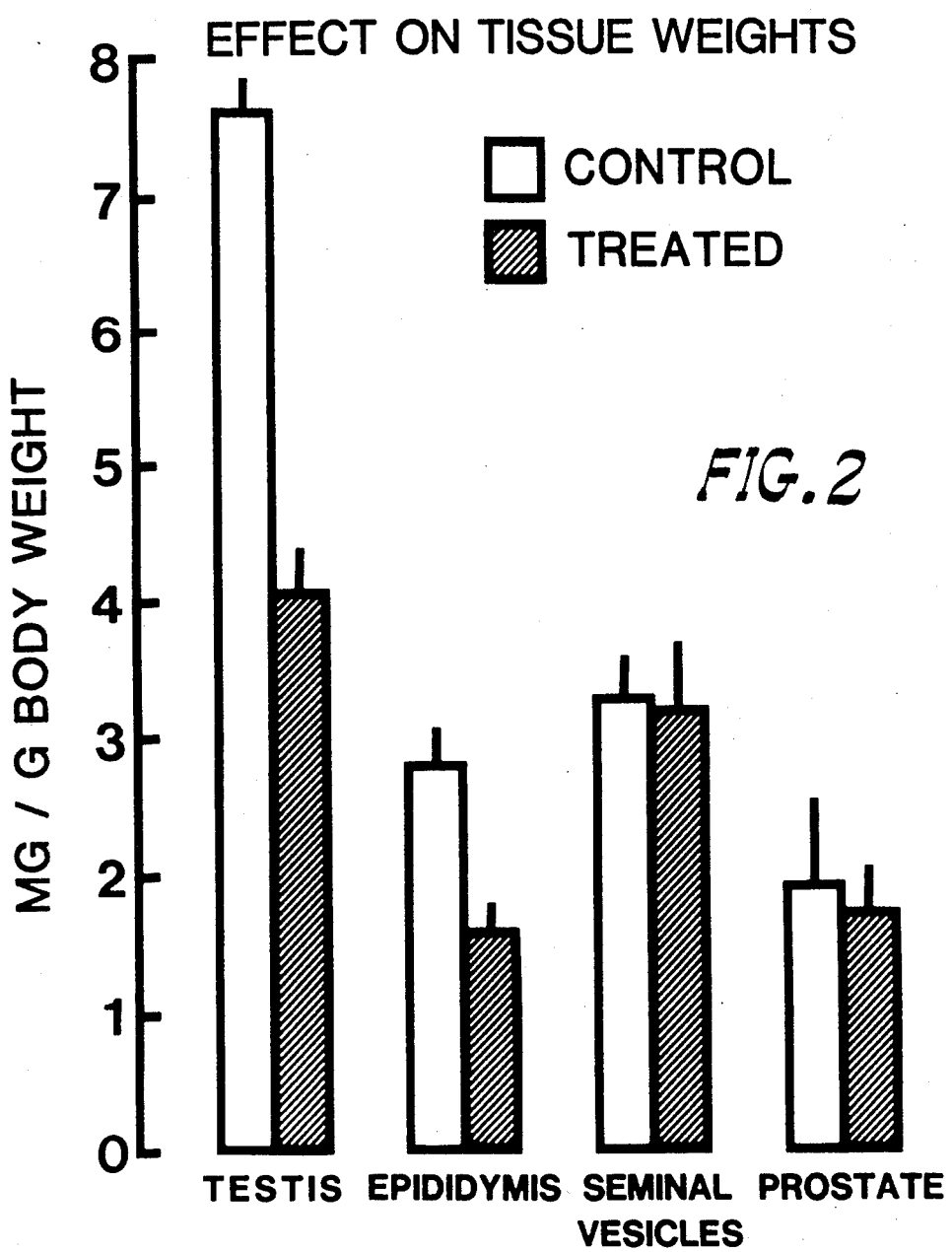
FIG. 2 is a bar graph illustrating the effect of the treatment on tissue weights.

FIG. 2 is a bar graph representation of typical experimental results, showing the effect of the treatment on tissue weights in milligrams per gram of body weight.

Figure 3:
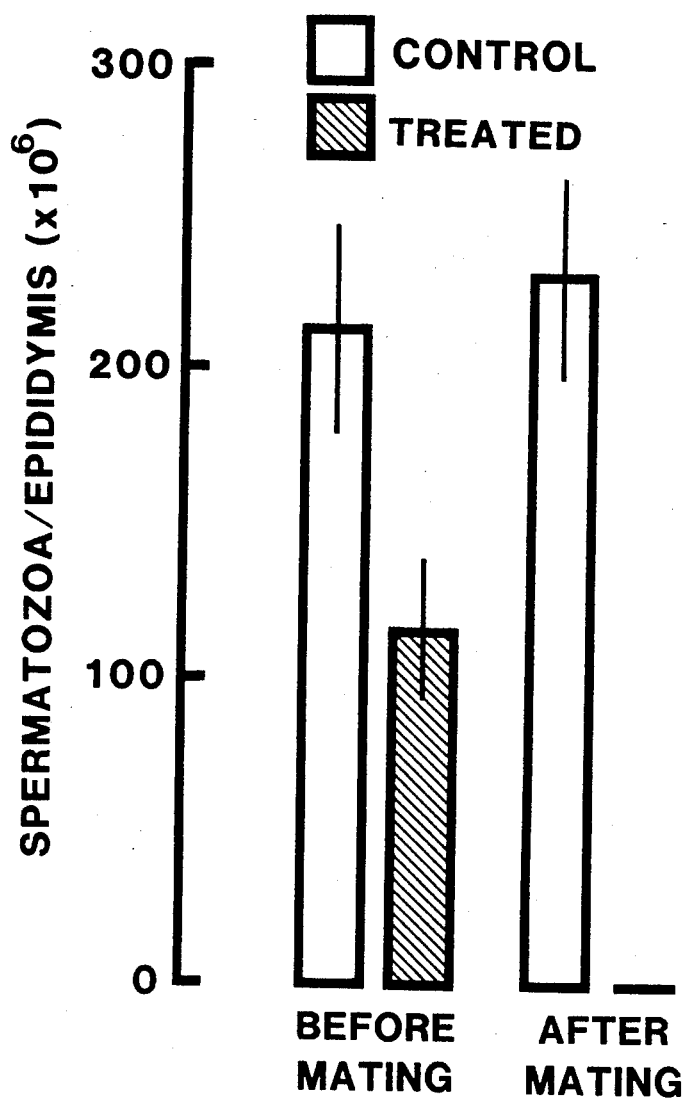
FIG. 3 is a bar graph showing the number of sperm in the epididymides before and after mating of treated and untreated (control) rats.

FIG. 3 is a bar graph representation of typical epididymal sperm counts of treated and control animals before and after matings.

The two primary functions of the testes are spermatogenesis and steroidogenesis. Although spermatogenesis was markedly suppressed by the THP treatment, Table 2 below shows that steroidogenesis was not significantly affected. The activities of the four major enzymes shown in the table increased significantly when calculated on a per mg protein basis. However, when calculated on a per gonad basis, there are no significant differences in activities between Control and Treated testes.

TABLE 2

Effect of THP Treatment on Steroidogenesis

| Steroid enzyme | Microunits/mg protein | | Microunits/testis pair | |
|---|---|---|---|---|
| | Control | Treated | Control | Treated |
| 20-alpha-HSD | 8.64 ± 1.33 | 19.67 ± 2.01 | 1465 ± 224 | 1475 ± 150 |
| 17-alpha-hydroxylase | 27.22 ± 4.68 | 61.91 ± 18.82 | 4600 ± 790 | 4643 ± 1411 |
| $C_{17-20}$-lyase | 16.60 ± 3.31 | 38.19 ± 9.11 | 2805 ± 559 | 2864 ± 683 |
| 17-beta-HSD | 15.29 ± 2.96 | 28.37 ± 5.69 | 2584 ± 500 | 2127 ± 427 |
| Androgen produced | 0.61 ± 0.32 | 1.33 ± 0.3 | 101.4 ± 28.9 | 107.9 ± 24.3 |

Sixteen male rats (96–100 days old) were used for this study. Half were injected intratesticularly with sterile-filtered distilled water (Control) and half with THP/water (7:3) solution (Treated). Nine weeks later the gonads were removed and homogenized; and enzyme activity was determined. One microunit equals 1 picomole of steroid converted or produced per minute. Androgen produced is the total $^{14}$C-labelled testosterone and androstenedione produced by homogenate in 30 minutes.

Figure 4:
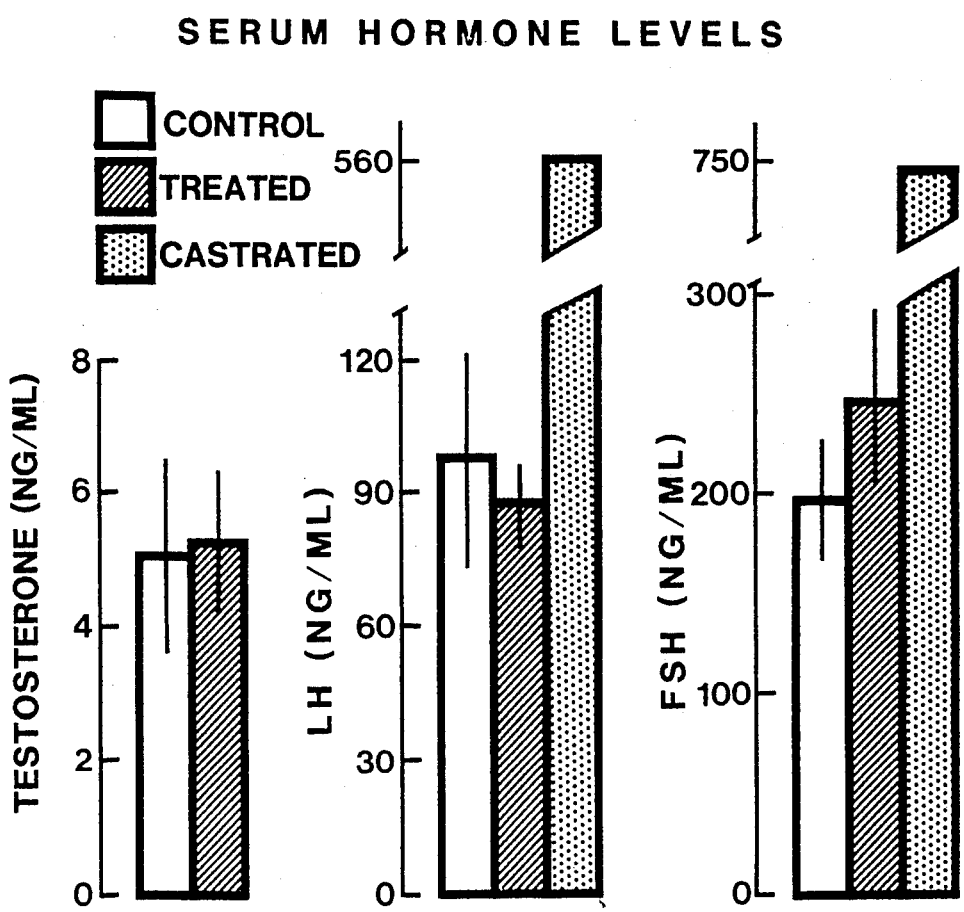
FIG. 4 is a bar graph showing the effect of the treatment on serum hormone levels.

As can be seen from Table 3 below, the serum levels of LH and FSH were not significantly altered by the THP treatment, in contrast to castration which resulted in marked increases. This is also illustrated in FIG. 4.

TABLE 3

Effect of THP treatment on serum LH, FSH, and testosterone levels

| | Control | Treated | Castrated Males | Young Females |
|---|---|---|---|---|
| Testosterone | 5.01 ± 1.4 | 5.21 ± 1.08 | N.D. | N.D. |
| LH | 97.5 ± 25.9 | 86.7 ± 8.7 | 560 | 33.5 ± 16.8 |
| FSH | 197.5 ± 21.9 | 255.0 ± 38.1 | 740 | 192.2 ± 35.9 |

Serum was collected from Control and Treated rats described in Table 2. Values for Control and Treated rats are means ± SEM (n = 3). Values for castrated males are the means for two adult rats. Values for young females are means ± SEM (n = 9) for 21-day old female rats. All values are in ng/ml serum. ND = not determined.

The amount of androgen (testosterone and androstenedione) produced in vitro from progesterone by the testes (Table 2) and the amounts of serum androgen (Table 3) are the same in Treated and Control animals, and the weights of the androgen-dependent prostates and seminal vesicles were not changed (Table 1).

Figure 5:
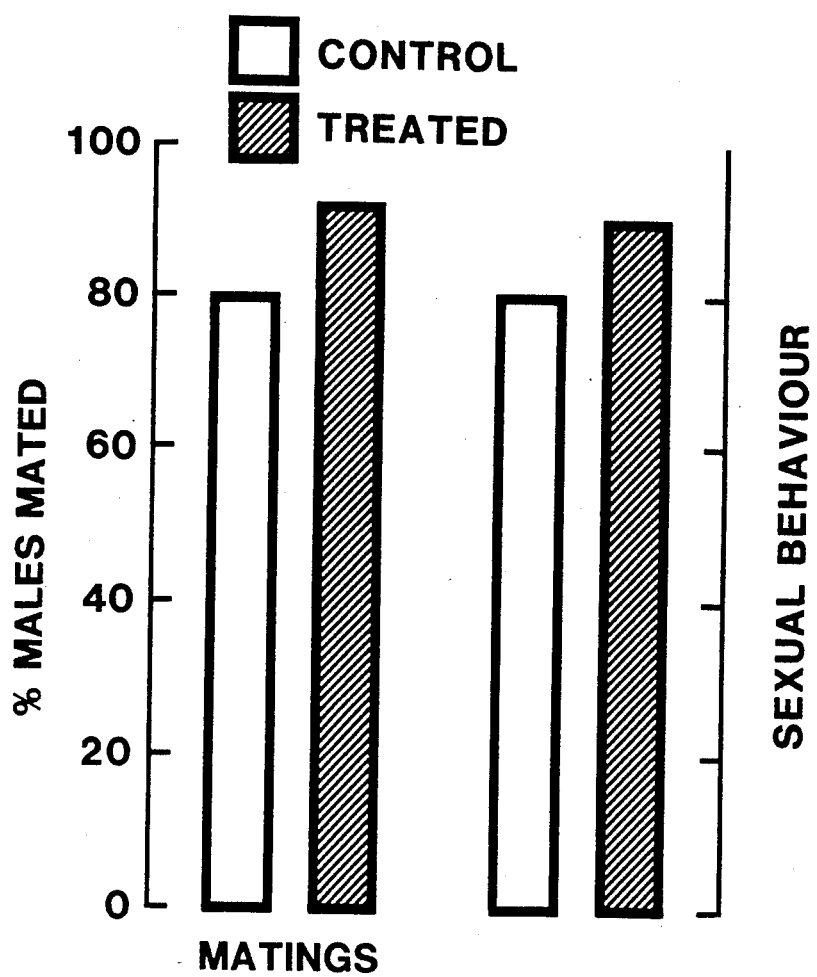
FIG. 5 is a bar graph showing the effect on libido.

Mating studies showed that Treated males exhibit the same level of sexual behaviour as the Controls, when caged with virgin females, and that they mate with the same frequency, as shown in Table 4 below and in FIG. 5. However, the fertility of the Treated males declined markedly by the 3rd mating and all Treated males were shown to be infertile by the 4th mating, as shown in Table 4 and FIG. 6. The fertility of the Treated males following the initial matings may be explained by the presence of viable spermatozoa stored in the epididymides. Since the spermatozoa can not be replenished by the spermatogenetically inactive testes, the animals are infertile after the stored sperm in the epididymides are depleted, following several matings.

Figure 6:
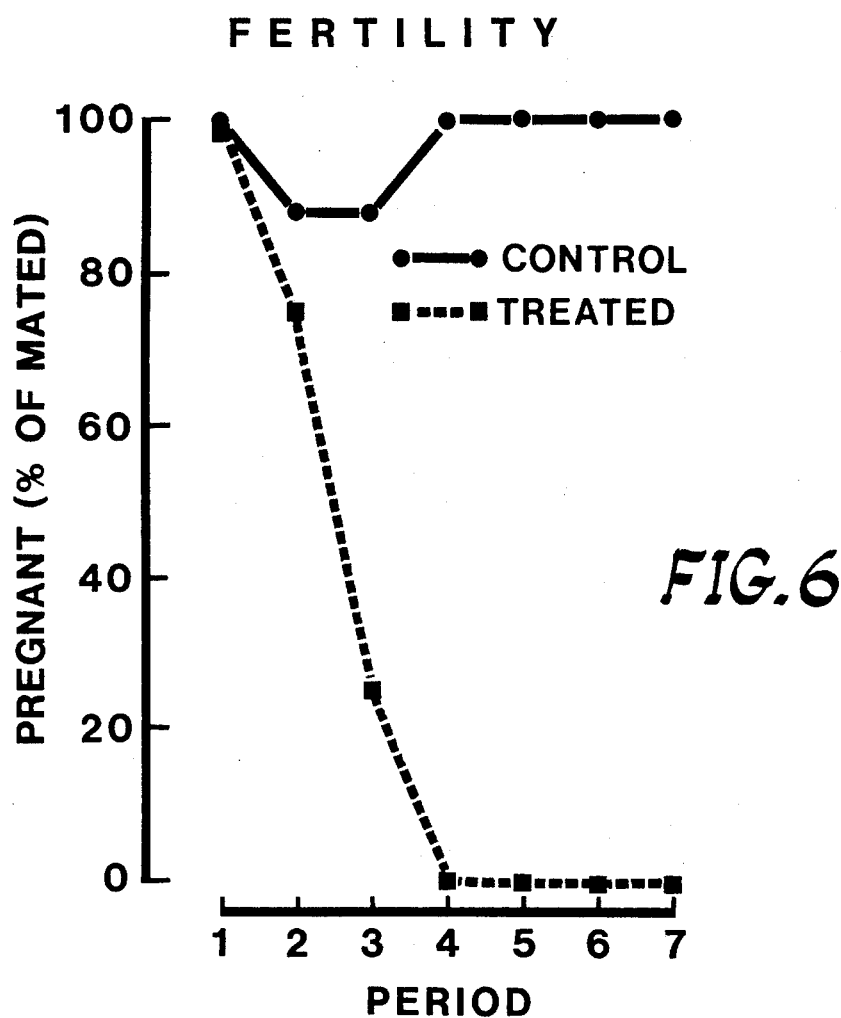
FIG. 6 is a graph illustrating the effect of the treatment on fertility.

Periods 1 through 5 in Table 4 and in FIG. 6 represent 2 through 6 weeks respectively after injection. However, there was a substantial lapse of time thereafter, prior to periods 6 and 7 in FIG. 6. Periods 6 and 7 represent 20 and 21 weeks respectively after injection, indicating no resumption of fertility even after 21 weeks.

TABLE 4

Effect of THP Treatment on Mating Frequency and on Fertility

| | Control | | Treated | |
|---|---|---|---|---|
| Period of cohabitation | Number mated | Number pregnant | Number mated | Number pregnant |
| 1 | 7 | 6 | 7 | 6 |
| 3 | 8 | 7 | 8 | 2 |
| 4 | 7 | 7 | 9 | 0 |
| 5 | 8 | 8 | 8 | 0 |

Male rats (n = 10), 80–90 days old at the start of the experiment, were treated as in Table 1, with either water (Control) or THP/water (7:3) solution (Treated). Two weeks later a virgin female rat was placed with each male for a period of 5 days (Monday to Friday). The appearance of a vaginal plug was taken as evidence that mating had occurred. The procedure was repeated with fresh virgin females on 5 successive weeks (Periods 1–5). Pregnancy was assessed by examination of uteri 10 days after the end of each cohabitation.

It was concluded as a result of the experiments that THP, when applied intratesticularly, acts as a potent inhibitor of spermatogenesis, resulting in long term infertility without affecting libido, secondary sex characters, mating behaviour and hormone levels. This treatment exhibits specific and potent antispermatogenic action with no observed side-effects and no observed effects on other aspects of reproductive and hormonal biology.

The treatment is very selective for spermatogenesis, with no reduction in male hormone production, in secondary sex characteristics, libido, sexual arousal and behaviour and no significant alteration in serum hormone levels. The treatment appears to be highly specific for the germinal cells; according to all histological, histochemical and biochemical data, the steroid hormone producing cells in the testis remain unaffected by the treatment.

In contrast to vasectomy, the procedure requires no surgery and therefore would seem to be more suitable as a technique for mass application. Also, since it halts spermatogenesis, this procedure will not promote the epididymal sperm congestion, sperm cysts, and autoimmune reactions observed with vasectomy.

In contrast to castration, aseptic surgery is avoided, and there is no period of healing. Also, there is no removal of the source of male sex steroid hormones as is the case with castration.

It is not yet known if the treatment is reversible, and it has not yet been verified that the treatment is effective in all mammals. Experiments in progress with hamsters indicate that the treatment is just as effective in this species as in the rat: within two weeks after a single injection, weights of the testes and epididymides were reduced by 37 to 43 percent, and the number of sperm stored in epididymides was decreased by 75 percent in the THP treated, unmated hamsters. Experiments on rabbits and primates are to follow, and are reasonably expected to show equally successful results.

It will be appreciated that the above description of the invention is a description of the state of knowledge to date with respect to the invention. Examples are given for the purpose of illustration only. Many variations on the details of the description may be possible, particularly but not exclusively with respect to solution strengths and dosage levels. Such variations are clearly envisioned as being within the spirit and substance of the scope of the invention as defined and claimed, whether or not expressly claimed, since these variations may be developed through routine non-inventive experimentation given the teachings of this disclosure.

What is claimed as the invention is:

1. A method of male contraception comprising injecting a suitable quantity of 1,2,2-trihydroxypropane in a suitable pharmaceutical carrier into the testes.

2. A method of male contraception as recited in claim 1, in which said carrier is distilled water.

3. A method of male contraception as recited in claim 2, in which the ratio of distilled water to 1,2,3-trihydroxypropane is approximately 3:7.

4. A method of male contraception as recited in claim 1, in which said carrier is a 0.9 percent saline solution.

5. A method of male contraception as recited in claim 4, in which the ratio of saline solution to 1,2,3-trihydroxypropane is approximately 3:7.

6. A method of male contraception as recited in claim 1, in which said carrier is a 0.9 percent saline solution and ethanol in a saline to ethanol ratio of approximately 12:1.

7. A method of male contraception as recited in claim 6, in which the ratio of saline to 1,2,3-trihydroxypropane to ethanol is approximately 3:7:0.25.

8. A method of male contraception as recited in claim 1, in which said carrier is distilled water and ethanol in a distilled water to ethanol ratio of approximately 12:1.

9. A method of male contraception as recited in claim 8, in which the ratio of distilled water to 1,2,3-trihydroxypropane to ethanol is approximately 3:7:0.25.

* * * * *

UNITED STATES PATENT AND TRADEMARK OFFICE
CERTIFICATE OF CORRECTION

PATENT NO. : 4,720,507

DATED : January 19, 1988

INVENTOR(S) : John P. Wiebe

It is certified that error appears in the above-identified patent and that said Letters Patent is hereby corrected as shown below:

Column 8, Claim 1, line 2, "1,2,2-" should read --1,2,3- --.

Signed and Sealed this

Ninth Day of August, 1988

Attest:

DONALD J. QUIGG

*Attesting Officer*  *Commissioner of Patents and Trademarks*